US011872412B2

United States Patent
Vortman et al.

(10) Patent No.: US 11,872,412 B2
(45) Date of Patent: Jan. 16, 2024

(54) FREQUENCY OPTIMIZATION IN ULTRASOUND TREATMENT

(71) Applicants: Kobi Vortman, Haifa (IL); Shuki Vitek, Haifa (IL); Eyal Zadicario, Tel Aviv-Jaffa (IL)

(72) Inventors: Kobi Vortman, Haifa (IL); Shuki Vitek, Haifa (IL); Eyal Zadicario, Tel Aviv-Jaffa (IL)

(73) Assignee: INSIGHTEC, LTD., Tirat Carmel (IL)

( * ) Notice: Subject to any disclaimer, the term of this patent is extended or adjusted under 35 U.S.C. 154(b) by 620 days.

(21) Appl. No.: 16/112,150

(22) Filed: Aug. 24, 2018

(65) Prior Publication Data
US 2019/0009109 A1 Jan. 10, 2019

Related U.S. Application Data

(63) Continuation of application No. 14/771,894, filed as application No. PCT/IB2014/000920 on Mar. 6, 2014, now abandoned.
(Continued)

(51) Int. Cl.
*A61N 7/00* (2006.01)
*A61N 7/02* (2006.01)
*A61B 90/00* (2016.01)

(52) U.S. Cl.
CPC .............. *A61N 7/00* (2013.01); *A61N 7/02* (2013.01); *A61B 2090/374* (2016.02); *A61N 2007/0073* (2013.01); *A61N 2007/0078* (2013.01)

(58) Field of Classification Search
CPC ...... A61B 2090/374; A61N 2007/0073; A61N 2007/0078; A61N 7/02
See application file for complete search history.

(56) References Cited

U.S. PATENT DOCUMENTS

| 3,746,427 A | 7/1973 | Foster |
| 4,995,693 A | 2/1991 | Wilson |

(Continued)

FOREIGN PATENT DOCUMENTS

| CN | 101090670 A | 12/2007 |
| CN | 101583322 A | 11/2009 |

(Continued)

OTHER PUBLICATIONS

International Search Report and Written Opinion dated Oct. 10, 2014 for International Application No. PCT/IB2014/000920 (16 pages).

(Continued)

*Primary Examiner* — Boniface Ngathi
*Assistant Examiner* — Milton Truong
(74) *Attorney, Agent, or Firm* — Morgan, Lewis & Bockius LLP (57) ABSTRACT

A system and method for selecting a patient-specific frequency for ultrasound therapy of a target within the patient are provided. The method includes: (a) for at least one segment of an ultrasound transducer and for each of a plurality of ultrasound frequencies within a test range, sonicating the target and measuring a parameter correlated with an amount of ultrasound energy absorbed in the target; and (b) for each said at least one segment, selecting for subsequent ultrasound therapy, among the frequencies within the test range, a frequency corresponding to a value of the measured parameter that itself corresponds to a maximum amount of ultrasound energy absorbed in the target.

8 Claims, 9 Drawing Sheets

Related U.S. Application Data (60) Provisional application No. 61/773,394, filed on Mar. 6, 2013.

(56) References Cited

U.S. PATENT DOCUMENTS

| | | | |
|---|---|---|---|
| 6,307,799 B1 | 10/2001 | Ngoi et al. | |
| 2002/0095087 A1 | 7/2002 | Mourad et al. | |
| 2005/0249667 A1* | 11/2005 | Tuszynski | A61B 8/08 |
| | | | 424/9.3 |
| 2005/0253056 A1 | 11/2005 | Nakata | |
| 2007/0279637 A1 | 12/2007 | Hill | |
| 2008/0208084 A1* | 8/2008 | Horzewski | H04N 1/387 |
| | | | 601/2 |
| 2009/0062724 A1* | 3/2009 | Chen | A61N 7/00 |
| | | | 604/22 |
| 2009/0116359 A1 | 5/2009 | Hendriks et al. | |
| 2010/0160837 A1* | 6/2010 | Hunziker | A61N 7/00 |
| | | | 601/2 |
| 2010/0185067 A1 | 7/2010 | Gupta | |
| 2010/0198064 A1* | 8/2010 | Perl | A61H 23/0245 |
| | | | 600/439 |
| 2011/0094288 A1* | 4/2011 | Medan | A61B 8/587 |
| | | | 324/307 |
| 2011/0319793 A1* | 12/2011 | Hynynen | A61N 7/02 |
| | | | 601/2 |
| 2012/0209150 A1* | 8/2012 | Zeng | A61N 7/02 |
| | | | 601/2 |
| 2012/0296197 A1* | 11/2012 | Vahala | A61N 7/02 |
| | | | 600/411 |
| 2014/0058292 A1* | 2/2014 | Alford | A61N 1/0529 |
| | | | 601/2 |

FOREIGN PATENT DOCUMENTS

| | | |
|---|---|---|
| EP | 0734742 A2 | 10/1996 |
| WO | 2006018837 A2 | 2/2006 |
| WO | WO2008099376 A2 | 8/2008 |
| WO | WO2012006053 A1 | 1/2012 |

OTHER PUBLICATIONS

Insightec, Ltd., First Office Action, CN201480025763.X, dated Dec. 5, 2017, 20 pgs.
Insightec, Ltd., Notification of Grant, CN201480025763.X, dated Jan. 22, 2019, 1 pg.
Insightec, Ltd., et al., Communication Pursuant to Article 94(3) EP14742349.5, dated Nov. 23, 2017, 6 pgs.
Insightec, Ltd., et al., Decision to Grant, EP14742349.5, dated Aug. 5, 2021, 2 pgs.
Notice of Reasons for Rejection, JP2015-560804, dated Jun. 22, 2018, 7 pgs.
Notice of Allowance, JP2015-560804, dated Oct. 12, 2018, 3 pgs.
Vortman, Office Action, U.S. Appl. No. 14/771,894, dated Jul. 10, 2018, 25 pgs.

* cited by examiner

FREQUENCY OPTIMIZATION IN ULTRASOUND TREATMENT

CROSS-REFERENCE TO RELATED APPLICATION

This is a continuation of U.S. patent application Ser. No. 14/771,894 (filed on Sep. 1, 2015) which claims priority to and the benefit of International (PCT) Patent Application Serial No. PCT/IB2014/000920 (filed Mar. 6, 2014), which claims the benefit of U.S. Provisional Patent Application No. 61/773,394 (filed Mar. 6, 2013). The entire disclosure of each of these applications is hereby incorporated by reference.

TECHNICAL FIELD

The present invention relates, generally, to focused-ultrasound therapy, and more particularly to systems and methods for optimizing the ultrasound frequency for increased energy deposition at the target.

BACKGROUND

Focused ultrasound (i.e., acoustic waves having a frequency greater than about 20 kilohertz) can be used to image or therapeutically treat internal body tissues within a patient. For example, ultrasonic waves may be used to ablate tumors, eliminating the need for the patient to undergo invasive surgery. For this purpose, a piezo-ceramic transducer is placed external to the patient, but in close proximity to the tissue to be ablated (the "target"). The transducer converts an electronic drive signal into mechanical vibrations, resulting in the emission of acoustic waves (a process hereinafter referred to as "sonication"). The transducer may be shaped so that the waves converge in a focal zone. Alternatively or additionally, the transducer may be formed of a plurality of individually driven transducer elements whose phases (and, optionally, amplitudes) can each be controlled independently from one another and, thus, can be set so as to result in constructive interference of the individual acoustic waves in the focal zone. Such a "phased-array" transducer facilitates steering the focal zone to different locations by adjusting the relative phases between the transducers. Magnetic resonance imaging (MM) may be utilized to visualize the focus and target in order to guide the ultrasound beam.

Figure 1:
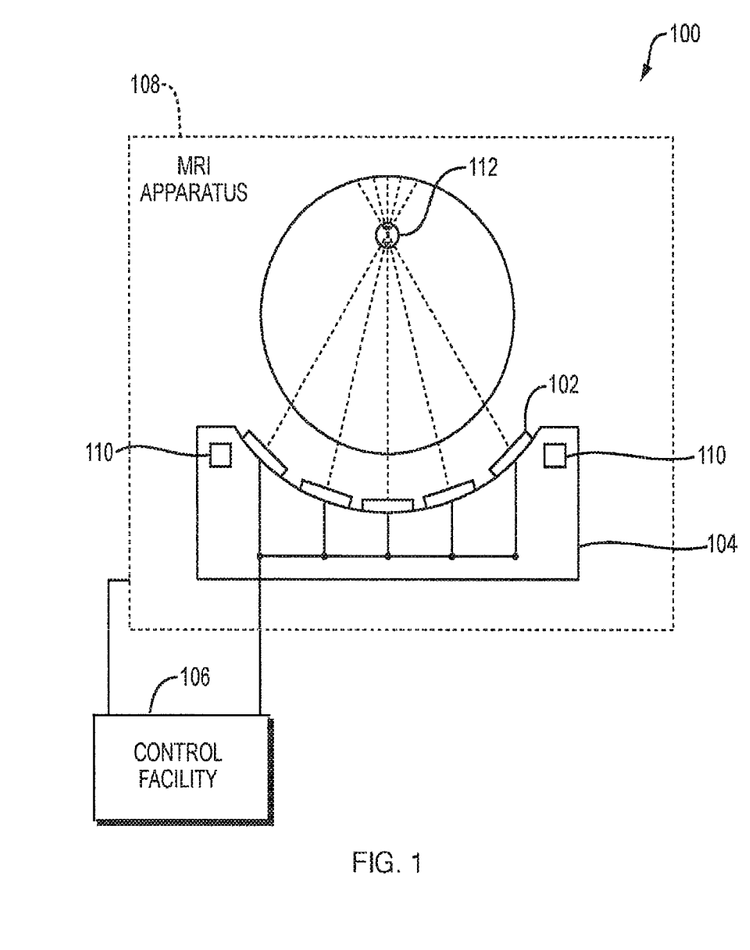
FIG. 1 schematically illustrates an MM-guided focused ultrasound system in accordance with various embodiments.

FIG. 1 illustrates an exemplary MM-guided focused-ultrasound system 100. The system 100 includes a plurality of ultrasound transducer elements 102, which are arranged in an array at the surface of a housing 104. The array may comprise a single row or a matrix, or generally any arrangement, of transducer elements 102. The array may have a curved (e.g., spherical or parabolic) shape, as illustrated, or may include one or more planar or otherwise shaped sections. Its dimensions may vary, depending on the application, between millimeters and tens of centimeters. The transducer elements 102 may be piezoelectric ceramic elements, or be made of piezo-composite materials or any other materials capable of converting electrical energy to acoustic energy. To damp the mechanical coupling between the elements 102, they may be mounted on the housing 104 using silicone rubber or any other suitable damping material.

The transducer elements 102 are driven via separate drive channels by a control facility 106. For n transducer elements 102, the control facility 106 may contain n control circuits each comprising an amplifier and a phase delay circuit, with each control circuit driving one of the transducer elements 102. The control facility may split a radio-frequency (RF) input signal, typically in the range of 0.1 MHz to 4 MHz, into n channels for the n control circuits. In conventional systems, the control facility 106 is configured to drive the individual transducer elements 102 of the array at the same frequency, but at different phases and different amplitudes so that they collectively produce a focused ultrasound beam at a desired location. The control facility 106 desirably provides computational functionality, which may be implemented in software, hardware, firmware, hardwiring, or any combination thereof, to compute the required phases and amplitudes for a desired focus location; these phase/amplitude computations may include corrections that compensate for aberrations resulting from ultrasound reflection or refraction at tissue interfaces or propagation in tissue having various acoustic parameters, which may be determined based, e.g., on computer tomography (CT) or other images of the anatomical region of interest. In general, the control facility 106 may include several separable apparatus, such as a frequency generator, a beamformer containing the amplifier and phase delay circuitry, and a computer (e.g., a general-purpose computer) performing the computations and communicating the phases and amplitudes for the individual transducers 102 to the beamformer. Such systems are readily available or can be implemented without undue experimentation.

The system 100 further includes an MRI apparatus 108 in communication with the control facility 106. An exemplary apparatus 108 is illustrated in more detail in FIG. 2. The apparatus 108 may include a cylindrical electromagnet 204, which generates a static magnetic field within a bore 206 of the electromagnet 204. During medical procedures, a patient is placed inside the bore 206 on a movable support table 208. A region of interest 210 within the patient (e.g., the patient's head) may be positioned within an imaging region 212 wherein the magnetic field is substantially homogeneous. A radio-frequency (RF) transmitter coil 214 surrounding the imaging region 212 emits RF pulses into the imaging region 212, and receives MR response signals emitted from the region of interest 210. The MR response signals are amplified, conditioned, and digitized into raw data using an image-processing system 216, and further transformed into arrays of image data by methods known to those of ordinary skill in the art. Based on the image data, a treatment region (e.g., a tumor) is identified. The ultrasound phased array 220, disposed within the bore 206 of the MM apparatus and, in some embodiments, within the imaging region 212, is then driven so as to focus ultrasound into the treatment region. The MRI apparatus 108 facilitates visualizing the focus 112 based on an effect it has on the sonicated tissue. For example, any of a variety of MRI-based thermometry methods may be employed to observe the temperature increase resulting from ultrasound absorption in the focus region. Alternatively, MR-based acoustic radiation force imaging (ARFI) may be used to measure the tissue displacement in the focus. Such measurements of the focus can serve as feedback for driving the ultrasound transducer array 220.

The goal of focused-ultrasound treatment is generally to maximize the amount of energy absorbed at the target while minimizing the exposure of healthy tissue surrounding the target, as well as tissues along the path between transducer and target, to ultrasound. The degree of ultrasound absorption in tissue is a function of frequency, given by:

$$I = I_0 e^{-2\alpha f z} \qquad (1),$$

where $I_0$ is the ultrasound intensity at the point of entry into the tissue (measured in W/cm$^2$), I is the intensity after beam propagation through the tissue over a distance z (which is measured in cm), f is the frequency of the ultrasound (measured in MHz), and α is the absorption coefficient at that frequency (measured in cm$^{-1}$·MHz$^{-1}$). The higher the product αf, the greater the degree of absorption in the target region will be, but the higher will also be the fraction of ultrasound that is absorbed on the way to, and therefore never reaches, the target region. This trade-off can be captured by the fraction $E_T$ of ultrasound energy absorbed along 1 cm of target tissue at a tissue depth z (i.e., after beam propagation through a distance z of the tissue):

$$E_T = e^{-2\alpha fz}(1 - e^{-2\alpha f \cdot 1cm}) \qquad (2).$$

Figure 3:
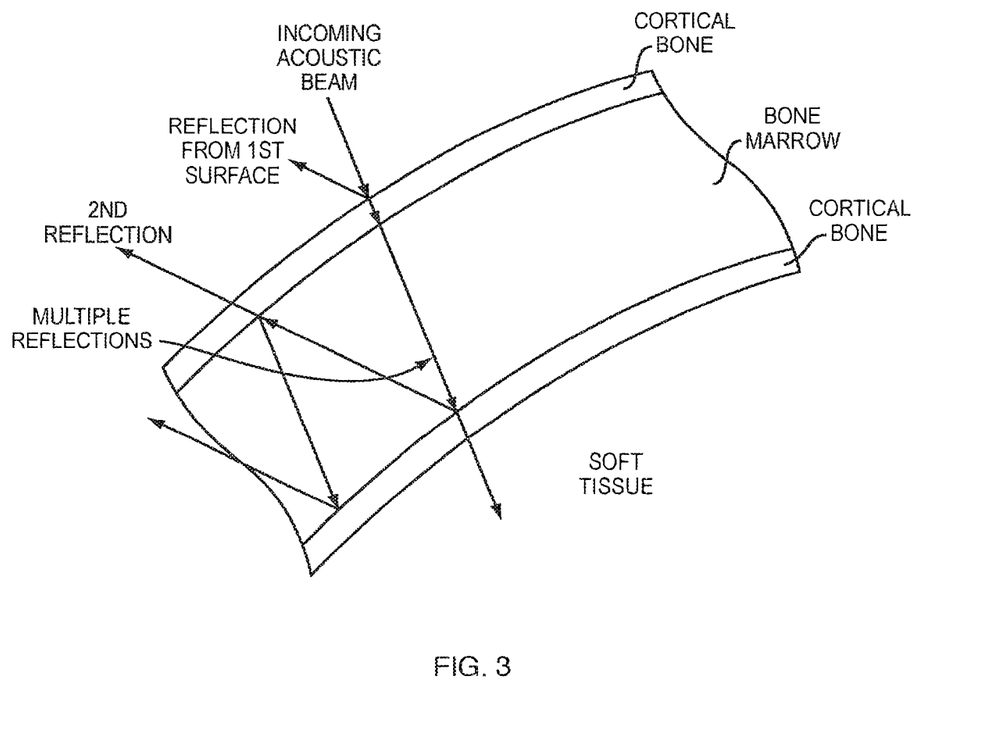
FIG. 3 illustrates reflection of ultrasound by tissue boundaries located between the transducer and the treatment target in a brain-treatment scenario.

In conventional ultrasound treatment procedures, the ultrasound frequency is selected based on the above relation to maximize $E_T$. This approach, however, fails to account for the effect of other ultrasound-tissue interactions that affect the energy deposition at the focus, such as reflection, refraction, and scattering. In some circumstances, such interactions are substantial; for example, when focusing ultrasound into the brain, the beam can be subject to multiple reflections off and between the cortical layers, as illustrated in FIG. 3. Accordingly, the ability to refine the frequency selection in order to improve energy deposition at the target would improve the performance and safety of ultrasound treatment.

SUMMARY

The present invention relates to focused-ultrasound treatment methods that involve determining an optimal frequency—i.e., one that maximizes the absorption or the acoustic intensity at the target—within a certain frequency range, as well as systems for implementing such methods. (The terms "optimal," "optimizing," "maximum," "maximizing", etc., as used herein, generally involve a substantial improvement (e.g., by more than 10%, more than 20%, or more than 30%) over the prior art, but do not necessarily mean that they achieve the best theoretically possible frequency, energy absorption, etc. Rather, optimizing the frequency, or maximizing the energy at the target, involves selecting the best frequency practically discernible within the limitations of the utilized technology and method.) The invention is based on the recognition that the amount of ultrasound energy absorbed at the target site is greatly affected by tissue interaction mechanisms other than absorption, and can be significantly improved by selecting an ultrasound frequency that deviates from the conventionally calculated absorption-based frequency.

Accordingly, embodiments of the present invention take multiple ultrasound-tissue interactions into account in selecting the treatment frequency. In principle, this can be accomplished computationally, by simulating the interactions of the ultrasound beam with the patient's tissues at various frequencies, using, for example, a finite-element method. The simulation may be based on a detailed tissue model as acquired, e.g., by computer tomography or ultra-short echo-time (TE) MRI; the model generally includes multiple tissue types or layers (e.g., for ultrasound focusing into the skull, layers of cortical bone, bone marrow, and soft brain tissue) and characterizes their respective material properties. It has been observed, however, that the optimal frequency varies greatly from person to person despite similar target sites, and often in a manner that either cannot be adequately captured with current tissue imaging and modeling techniques or is computationally so expensive as to be impractical. Therefore, in preferred embodiments, the optimal frequency is determined experimentally and individually for each patient. This may be done, prior to treatment, by measuring ultrasound absorption in the target (or a quantity indicative thereof) at several frequencies within a specified range (generally at energy levels low enough to not cause any damage to the tissue), and identifying the optimal frequency based on the measurements. This method accounts implicitly for all (known or unknown) contributing factors to the amount of ultrasound energy absorbed at the target. Alternatively, if a particular mechanism, such as reflection, is found to dominate the attenuation of ultrasound between the transducer and the target, the effect of that mechanism may be experimentally quantified, and the frequency selected so as to minimize the effect. For example, when focusing ultrasound into the brain, the beam can be subject to multiple reflections off and between the cortical layers; in this scenario, one way to optimize the frequency is to measure the total skull reflectance (summing over contributions from all the reflected beams), and selecting the frequency for which the reflected beam is minimized.

Accordingly, in one embodiment, the invention pertains to a patient-specific frequency-optimization method for ultrasound therapy of a target within the patient. The method involves sonicating the target and measuring (e.g., using thermometry) a parameter (e.g., power, energy, intensity, acoustic force, tissue displacement, and temperature) associated with the amount of ultrasound energy absorbed in the target for each of a plurality of ultrasound frequencies within a test range. In some embodiments, the transducer includes multiple segments (which may be defined, e.g., based at least in part on the patient's anatomy), and the parameter is measured for each test frequency and each segment. Among the frequencies within the test range, a frequency corresponding to the value of the measured parameter that itself corresponds to the maximum amount of ultrasound energy absorbed in the target is selected (for the entire transducer or each segment). In some embodiments, the plurality of frequencies within the test range is defined dynamically based, at least in part, on a value of the parameter measured for a previously tested frequency. Following frequency selection, the transducer (or transducer segments) may be driven at the selected frequency (or frequencies) and at a therapeutic energy level to thereby sonicate the target; the therapeutic energy level typically exceeds the energy level of sonications applied during testing. In multi-segment embodiments, the segments may be driven sequentially (e.g., cyclically) or simultaneously, each at its respective selected frequency.

A further aspect is directed to a system for selecting a patient-specific frequency for ultrasound therapy of a target within the patient. The system includes an ultrasound transducer and an associated controller capable of driving the transducer at any frequency within a test range of frequencies so as to sonicate the target, as well as a measurement facility (e.g., an MM apparatus) for measuring a parameter correlated with the amount of ultrasound energy absorbed in the target. The system further has a computational facility for (i) causing the ultrasound transducer controller to drive one or more segments of the transducer sequentially at each of a plurality of frequencies within the test range so as to sonicate the target, (ii) causing the measuring facility to measure a parameter correlated with the amount of ultrasound energy absorbed in the target for each of the frequencies, and (iii) for each of the segments, selecting for subsequent focused-ultrasound therapy, among the frequencies within the test range, a frequency corresponding to the value of the measured parameter that itself corresponds to a maximum amount of ultrasound energy absorbed in the target. In embodiments where the ultrasound transducer has a plurality of segments, the controller may be configured to cause the ultrasound transducer, during ultrasound therapy, to drive the segments together, each at its respective selected frequency. Alternatively, the segments may be driven sequentially, e.g., cyclically.

Yet another aspect provides a patient-specific frequency-optimization method for ultrasound therapy of a target that involves defining a plurality of segments within an ultrasound transducer array, and, separately for each of the segments, driving the segment successively at each of a plurality of frequencies within a test frequency range so as to sonicate the target. For each sonication, a parameter correlated with the amount of ultrasound energy absorbed in the target (e.g., power, energy, intensity, acoustic force, tissue displacement, and/or temperature) is measured for each frequency (e.g., using thermometry or acoustic radiation force imaging). The values of the parameter measured for the plurality of segments may be combined, for each of the plurality of frequencies, into a total parameter value correlated with the total amount of ultrasound energy absorbed in the target. Among the plurality of frequencies, the frequency corresponding to the value of the measured total parameter that itself corresponds to a maximum total amount of ultrasound energy absorbed in the target is then selected for subsequent therapy.

In a further aspect, a system for selecting a patient-specific frequency for ultrasound therapy of a target within the patient is provided. The system includes an ultrasound transducer comprising a plurality of segments and an associated controller capable of driving each of the transducer segments at any of a plurality of frequencies within a range of frequencies so as to sonicate the target, as well as a measurement facility (e.g., an MRI apparatus) for measuring a parameter correlated with an amount of ultrasound energy absorbed in the target (such as, e.g., tissue displacement). Further, the system includes a computational facility for (i) causing the ultrasound transducer controller to separately drive each of the segments sequentially at each of a plurality of frequencies within a test range so as to sonicate the target, (ii) causing the measurement facility to measure a parameter correlated with an amount of ultrasound energy absorbed in the target for each of the frequencies, (iii) for each of the plurality of frequencies, combining values of the parameter measured for the plurality of segments into a total parameter value correlated with the total amount of ultrasound energy absorbed in the target, and (iv) selecting for subsequent focused-ultrasound therapy, among the plurality of frequencies, an optimal frequency corresponding to the value of the measured total parameter that itself corresponds to the maximum total amount of ultrasound energy absorbed in the target. The controller may be configured to cause the ultrasound transducer, during ultrasound therapy, to drive the segments together at the selected optimal frequency.

BRIEF DESCRIPTION OF THE DRAWINGS

The foregoing and the following detailed description will be more readily understood when taken in conjunction with the drawings, in which.

DETAILED DESCRIPTION

Figure 2:
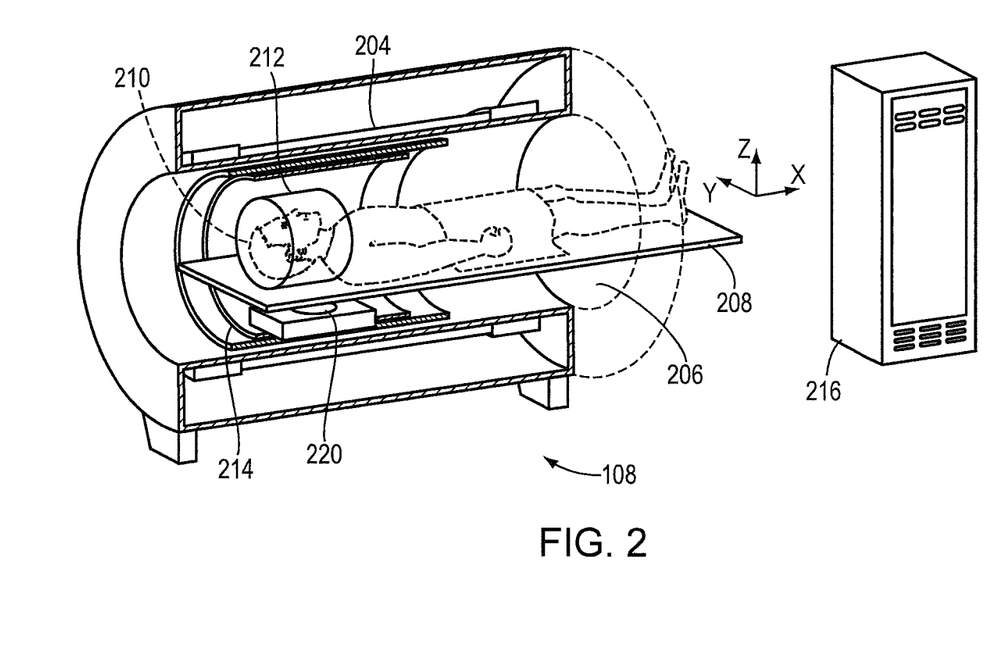
FIG. 2 illustrates an MM system in accordance with various embodiments.
Figure 4:
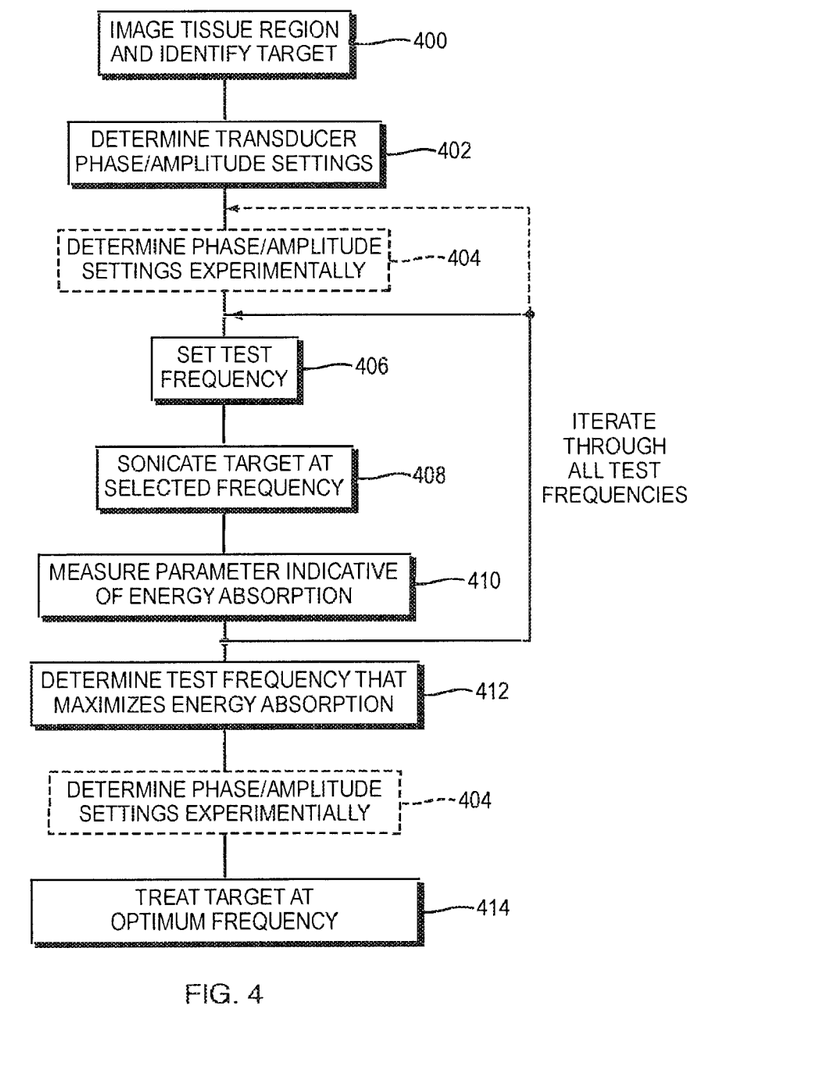
FIG. 4 is a flow chart illustrating a method for optimizing the sonication frequency in accordance with various embodiments.

In various embodiments, the present invention provides methods for optimizing the frequency of sonications in focused-ultrasound procedures for a particular patient; an exemplary method is illustrated in FIG. 4. After the treatment configuration has been set up and the patient has been placed in or relative to the ultrasound transducer and imaging apparatus 108 (e.g., as depicted in FIG. 2), images of the relevant tissue region may be acquired and processed to identify the target therein (step 400). Then, relative phase and/or amplitude settings of the ultrasound transducer elements 102 that result in a beam focused at the target may be computed based on the relative position of the transducer and target and any a-priori knowledge and/or image-derived information about the intervening tissues (step 402). The phase and/or amplitude settings may be refined experimentally before, after, and/or at one or more times during the frequency-optimization process based on observations of the focus quality and/or the focus location relative to the target (step 404); methods for computational and experimental phase/amplitude determinations and adjustments are well-known to those of skill in the art. The transducer is then driven in accordance with the determined phase and amplitude settings to sonicate the target.

To optimize the frequency of the ultrasound, the target is sonicated sequentially at different "test frequencies" within a "test range" of frequencies, and for each tested frequency, a parameter indicative of energy absorption in the target is measured. The test range may span the entire range of frequencies suitable for ultrasound treatment (e.g., in various embodiments, 0.1 MHz to 4 MHz), but is typically a much smaller sub-range thereof in which the optimal frequency is to be expected. Such a sub-range may be determined, e.g., based on computational estimates of the optimal frequency, the results of simulations, or empirical data acquired for the same organ or tissue in another patient. The frequencies to be tested may be distributed uniformly or non-uniformly over the test range. In various embodiments, the density of test frequencies increases with closer proximity to an estimated optimal frequency. The test range and the test frequencies therein may be predetermined, or adjusted dynamically during the optimization process. For example, in one embodiment, testing is initially performed at large frequency intervals (e.g., in steps of 20 kHz) over a large test range (e.g., from 600 to 750 kHz) to determine a sub-range of frequencies resulting in high energy absorption at the target, and the optimum frequency is thereafter determined within the sub-range by testing at smaller intervals (e.g., in steps of 10 kHz or 5 kHz). In another embodiment, testing is performed for a sub-set of pre-determined potential test frequencies, each actual test frequency being selected from the set of potential test frequencies based on the results of previous tests.

Thus, optimizing the frequency involves iteratively setting a test frequency (step 406), sonicating the target at the selected frequency (step 408), and quantitatively assessing the resulting energy absorption at the target (step 410) using, e.g., MRI thermometry to measure the temperature increase in the target resulting from the absorbed energy, MR-ARFI to measure the tissue displacement resulting from acoustic pressure at the target, ultrasound detection to measure the intensity of the ultrasound that is reflected (i.e., not absorbed), or generally any experimental technique for measuring a parameter that correlates with energy absorption at the target in a known and predictable manner. The maximum (in the case of, e.g., temperature or pressure) or minimum (in the case of, e.g., reflection) of the measured parameter is then determined to identify the test frequency at which energy absorption at the target is maximized (step 412). Following frequency optimization, the phase and/or amplitude settings of the phased-array transducer may be adjusted to optimize the focus for the selected frequency. Treatment may then commence at the optimum frequency and phase/amplitude settings (step 414).

Figure 5A:
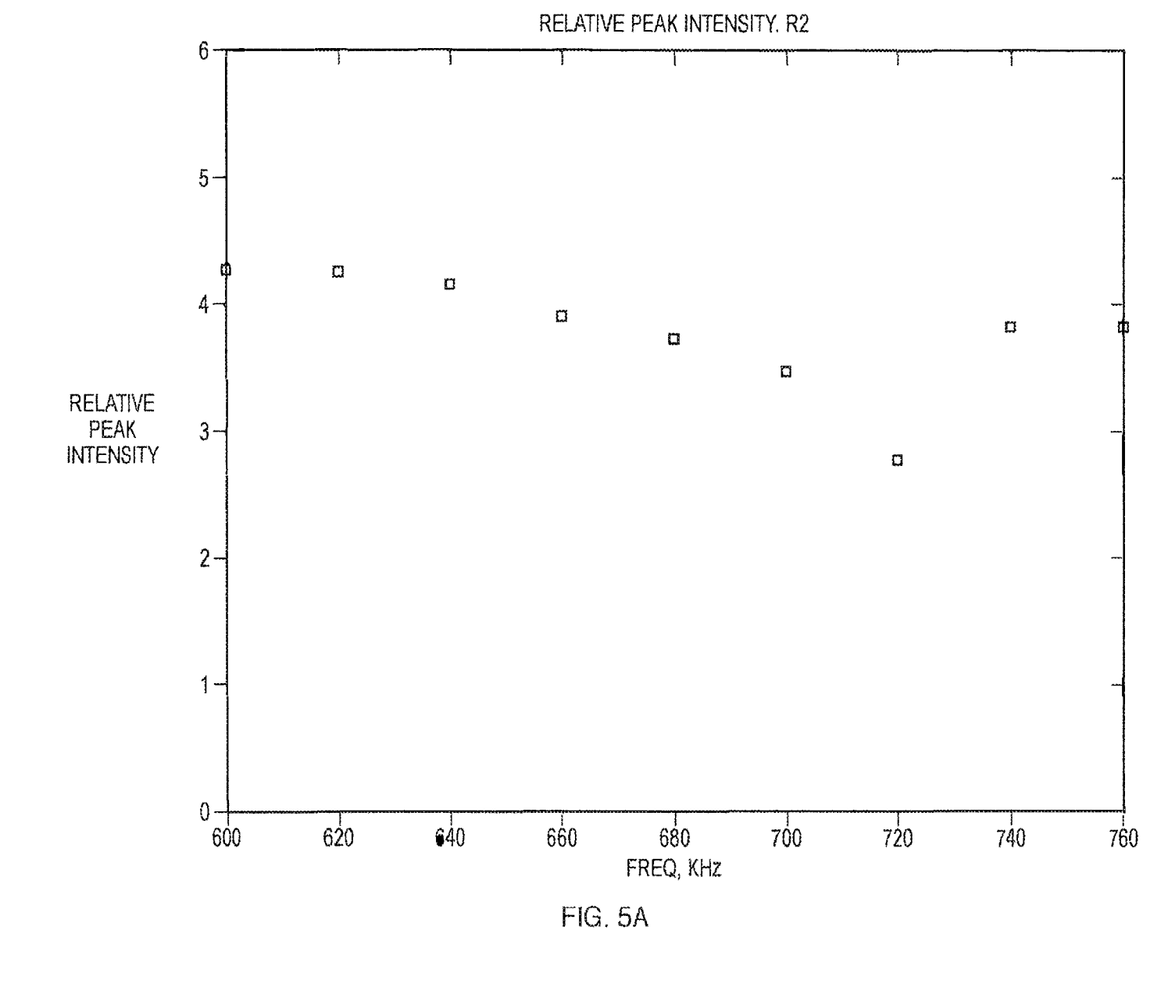
FIGS. 5A and 5B are graphs of the experimentally determined and the predicted dependence of energy absorption from the frequency for an exemplary treatment scenario.
Figure 5B:
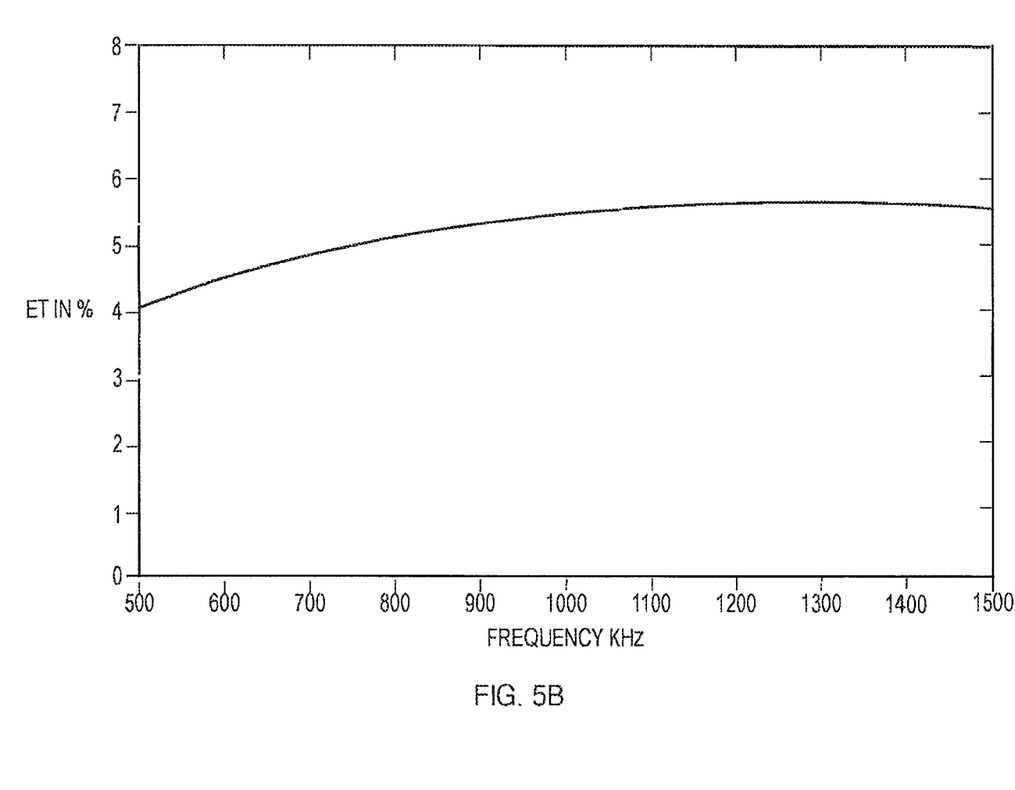

The utility of frequency optimization in accordance herewith derives from the fact that energy absorption varies significantly and often nonmonotonically with frequency and the optimum frequency for a particular patient is typically unpredictable. For example, FIG. 5A illustrates the ultrasound peak intensity measured at a number of frequencies between 600 kHz and 760 kHz for an ex-vivo skull by a hydrophone placed inside the skull. As shown, the peak intensity achieved at 600 kHz is about 50% higher than that at 720 kHz, and the peak intensity at 740 kHz is more than 30% higher than that at 720 kHz. Such large variations in intensity over short frequency ranges are surprising when compared to the intensity variation with frequency that results from absorption only, as modeled with equation (2). (FIG. 5B shows, for example, the fraction of energy $E_T$ absorbed at a 1 cm target located 6 cm inside soft tissue having an absorption coefficient of $\alpha=0.06$ Napiers/cm/MHz (which is approximated for brain tissue) using equation (2); as can be seen, the absorbed energy varies smoothly as a function of ultrasound frequency and does not contain a sudden drop such as the experimentally found minimum at 720 Hz reflected in FIG. 5A.) A similar measurement for a different skull may reveal similarly high variations in peak intensity, but generally with a different frequency-dependency (e.g., different frequencies at which the intensity is minimized or maximized).

In certain treatment scenarios, ultrasound waves propagating towards the target from different directions may encounter a highly variable anatomy, such as different thicknesses of tissue layers and different acoustic impedances. For example, during transcranial ultrasound treatment procedures, acoustic beams coming from different directions may encounter cortical skull bone of different thicknesses, bone marrow of different thicknesses, etc., as well as variability of absorption coefficients in the soft tissue. In various other clinical scenarios, some of the soft tissue may have much higher calcification contents than expected and, thus, a much higher attenuation in the near field. In these cases, overall energy deposition at the target may be improved by optimizing the frequency separately for different regions or segments of the transducer array, and then driving the transducer, simultaneously or sequentially, at multiple frequencies for the different segments, rather than at a single frequency for the whole transducer.

Figure 6:
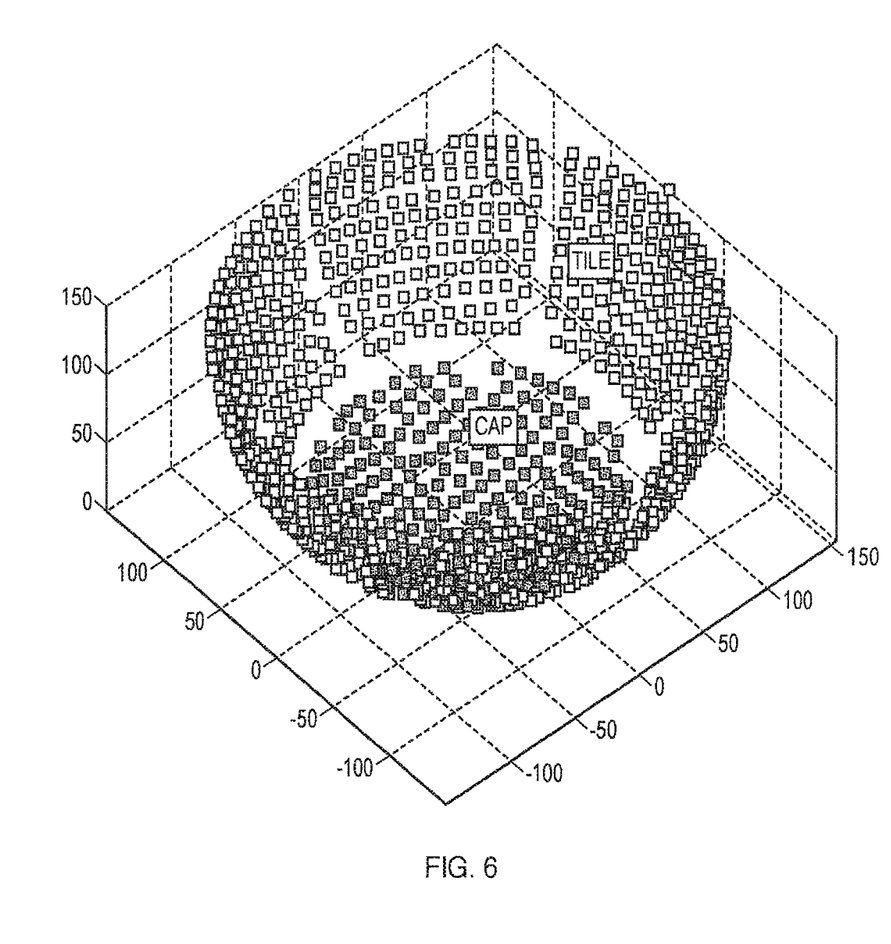
FIG. 6 illustrates partitioning of an ultrasound transducer for brain treatment in accordance with one embodiment.

The partitioning of the transducer array (or grouping of transducer elements) for such segment-based frequency optimization may be based on the similarity of the relevant paths through the anatomy for different transducer elements, the ability to generate a focus of sufficiently high quality with each transducer segment (which depends, e.g., on the total number of elements in the segment), and, ultimately, the combined therapeutic effect provided by all transducer segments. If, for example, the array is divided into too many segments that are too small (in an attempt to maximize the benefits of frequency optimization), the individual segments may fail to generate sufficiently sharp foci because they no longer have effective focusing ability, and the beam will disperse. FIG. 6 illustrates a suitable partitioning of an approximately semi-spherical transducer used for brain-tumor treatment. In the depicted embodiment, the transducer array is divided into seven segments, a central "cap" and six similarly sized surrounding "tiles." In general, the transducer may have more or fewer segments; typical transducer divisions include between three and fifteen segments.

Figure 7:
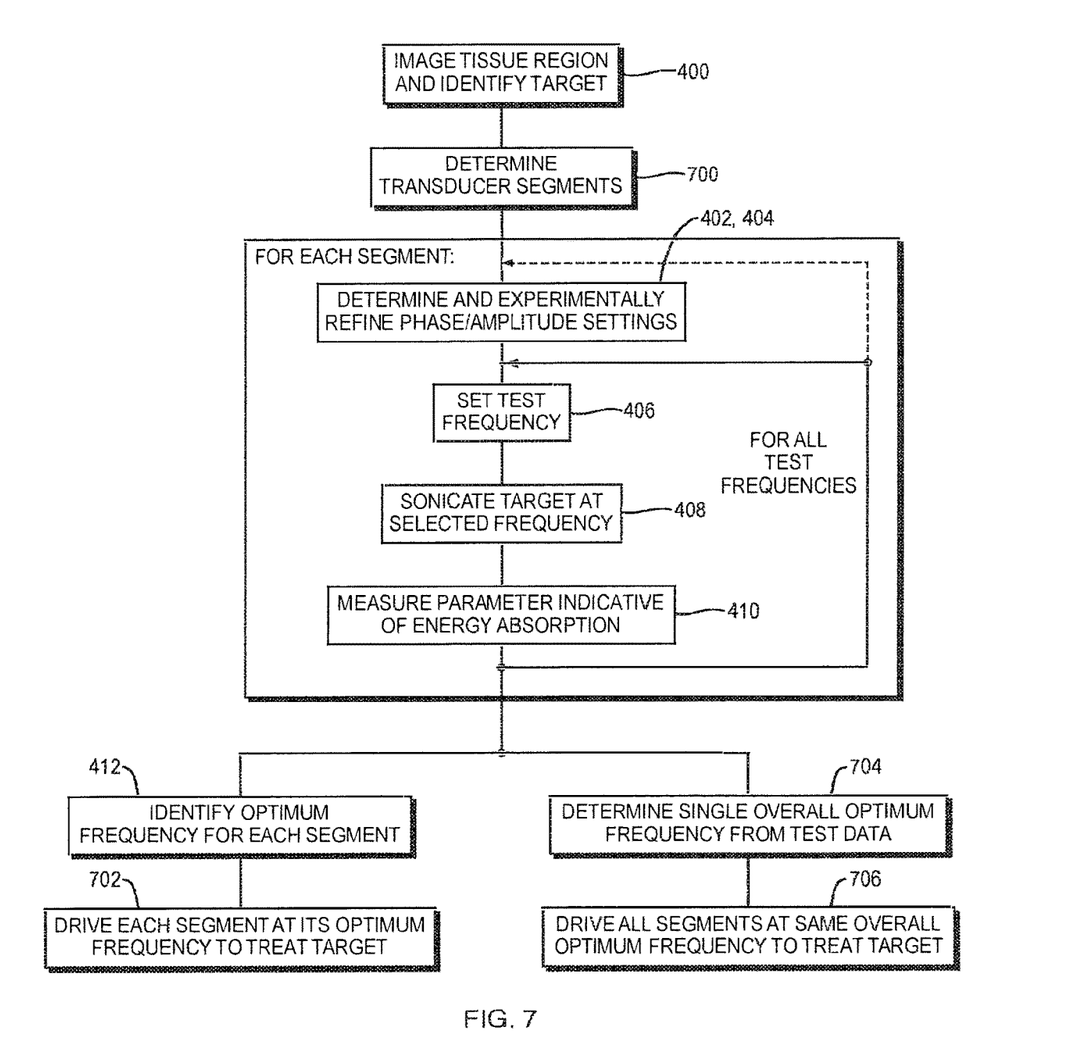
FIG. 7 is a flow chart illustrating a method for optimizing the sonication frequencies of multiple transducer segments separately in accordance with various embodiments.

FIG. 7 illustrates a method for optimizing the frequencies of a multi-segment transducer. After the target within the patient has been identified (e.g., based on images) in step 400 and the transducer segments have been defined (step 700), the focus of each segment may be separately optimized by setting and adjusting the relative phases and/or amplitudes between the transducer elements of that segment (steps 402, 404) so as to generate a high-quality focus at the target location, and further determining the frequency dependence, within a test range, of energy absorption at the target in the manner described above (steps 406, 408, 410). In some embodiments, the optimum frequency (i.e., the frequency that maximizes energy absorption at the target) is identified separately for each segment (step 412); to treat the target, the separately optimized transducer segments may then be driven sequentially or together, each at its own optimum frequency (step 702). For example, the segments may be driven separately and cyclically such that ultrasound from segments driven at different frequencies does not destructively interfere, and at the same time that energy deposited in the target does not significantly dissipate during each sonication cycle. In alternative embodiments, a single frequency that maximizes the overall absorption of ultrasound energy received from the various segments is inferred from the individual measured frequency dependencies in a manner explained further below (step 704), and the various segments, although tested separately, are all driven at that same, overall-optimal frequency during treatment (step 706). Driving the segments at a single, common frequency may, advantageously, result in a smaller focus with higher peak intensity as it ensures constructive interference of the ultrasound waves from different segments.

Various techniques can be used to measure energy absorption in the target—directly or indirectly via a related physical quantity—to then maximize the amount of energy absorbed via selection of an optimal frequency. One approach is to monitor the temperature at the target, which increases proportionally to the amount of energy absorbed. Thermometry methods may be based, e.g., on MM, and may utilize a system such as that depicted in FIG. 2, in conjunction with suitable image-processing software. Among various methods available for MR thermometry, the proton resonance frequency (PRF) shift method is often the method of choice due to its excellent linearity with respect to temperature change, near-independence from tissue type, and temperature map acquisition with high spatial and temporal resolution. The PRF shift method exploits the phenomenon that the MR resonance frequency of protons in water molecules changes linearly with temperature. Since the frequency change with temperature is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline PRF phase image prior to a temperature change and then to acquire a second phase image after the temperature change, thereby capturing a small phase change that is proportional to the change in temperature. A map of temperature changes may then be computed from the MR images by determining, on a pixel-by-pixel basis, phase differences between the baseline image and the treatment image, and converting the phase differences into temperature differences based on the PRF temperature dependence while taking into account imaging parameters such as the strength of the static magnetic field and echo time (TE) (e.g., of a gradient-recalled echo). Various alternative or advanced methods may be used to compensate for patient motion, magnetic-field drifts, and other factors that affect the accuracy of PRF-based temperature measurements; suitable methods known to those of skill in the art include, e.g., multibaseline and referenceless thermometry.

Using PRF-based or any other suitable thermometry method, the optimal ultrasound frequency within a specified range can be determined by driving the transducer successively at a number of different frequencies (e.g., at specified frequency intervals within the selected range), while keeping the power and duration (or, more generally, the total transmitted energy) the same, to focus ultrasound at the target site of a particular patient, and measuring the temperature increase at the target for each such sonication. This is done prior to treatment; thus, in order to avoid tissue damage, the ultrasound transducer is driven at much lower power than subsequently during treatment (while being high enough to obtain a meaningful signal-to-noise ratio). Further, to ensure the comparability of the measurements for different frequencies, each temperature increase is preferably measured against a similar baseline temperature. This can be accomplished by waiting a sufficient amount of time following each sonication to let the tissue cool back down to a temperature approximately equal to the baseline temperature and using sufficiently low energy such that effects on the tissue due to temperature changes are limited (e.g., clinically insignificant). When the temperature increase has been measured at the various discrete frequencies within the range of interest, the frequency for which the temperature increase is maximum is selected for operating the transducer during subsequent treatment. In embodiments where the frequency is optimized separately for multiple transducer segments, this procedure is performed for each segment. During treatment, the various segments may be driven together or alternately (e.g., cycling through the segments), each at its respective optimum frequency.

Another quantity usefully related to ultrasound energy absorption in tissue is the temporary local displacement of that tissue due to acoustic radiation pressure, which is highest at the focus (where the waves converge and highest intensity is achieved). The ultrasound pressure creates a displacement field that directly reflects the acoustic field. The displacement field can be visualized, using a technique such as MR-ARFI, by applying transient-motion or displacement-sensitizing magnetic field gradients to the imaging region by gradient coils, which are part of standard MRI apparatus (such as apparatus 108 depicted in FIG. 2) and are typically located near the cylindrical electromagnet 204. When the ultrasound pulse is applied in the presence of such gradients, the resulting displacement is directly encoded into the phase of the MR response signal. For example, the gradient coils and transducer may be configured such that the ultrasound pulse pushes material near the focus towards regions of the magnetic field with higher field strengths. In response to the resulting change in the magnetic field, the phase of the MR response signal changes proportionally, thereby encoding in the signal the displacement caused by the ultrasound radiation pressure. Further detail about MR-ARFI is provided in U.S. patent application Ser. No. 12/769,059, filed on Apr. 28, 2010, the entire disclosure of which is hereby incorporated herein by reference.

For a given transducer arrangement, the tissue displacement measured with MR-ARFI is directly proportional to the ultrasound intensity. Advantageously, the energies required to obtain good displacement signals are very small compared to typical therapeutic energies (and are achieved by sonication for very short periods, e.g., about 20 ms), rendering ARFI a suitable candidate for pre-treatment optimizations. However, the displacement forces generated by ultrasound waves coming from different directions partially cancel each other. Therefore, when using MR-ARFI to tune the frequency for maximum energy absorption at the focus, the frequency is preferably optimized separately for multiple transducer segments—each covering not too large a solid angle—even when a single frequency is selected in the end to drive the entire transducer array; the overall optimal frequency is derived from the optimal frequencies for the individual segments by combining them in a suitable manner (as explained below). (In contrast to radiation forces, thermal energies attributable to different segments and ultrasound wave directions accumulate without cancellations. Thus, when using thermometry for frequency optimization, the procedure may be performed on the transducer array as a whole.)

Since the purpose of various embodiments is to find the optimal treatment frequency for a specific patient by a procedure that is part of the treatment flow, that procedure is preferably short, e.g., on the order of several minutes. This is achievable with ARFI if neither the number of transducer segments nor the number of discrete frequencies tested is too large. For example, to determine the best frequency for a curved (e.g., hemispherical) ultrasound transducer used in brain tumor treatment, the transducer may be divided, e.g., into seven segments (a cap and six tiles, as illustrated in FIG. 6) or even in only four segments (a cap and three tiles). The segments may be defined based on generic criteria such as the solid angles they cover, or based on more detailed criteria regarding, e.g., the particular patient's anatomy. Tissue displacement may be measured for each segment at about ten different frequencies or less, for example, at nine frequencies at 20 kHz intervals within a range from 600 kHz to 760 kHz (as shown in FIG. 5A). Denoting the number of segments with Ns and the number of discrete frequencies with $N_f$, a total of $N_S \cdot N_f$ measurements are required.

For each segment, a single scan covering all frequencies may be performed at a lateral plane (or multiple, e.g., three, parallel planes) passing through the focus of that segment (which may be slightly displaced from the theoretical focus location achieved when all segments operate together). The MR scan is synchronized with ultrasound pulses that generate the tissue displacement. In some cases, the relative phases between the elements of the transducer segment are corrected, e.g., based on CT images or other a-priori knowledge, to compensate, e.g., for bone variability. Using a state-of-the-art focused-ultrasound/MR-ARFI system, this MR scan requires, in one embodiment, about 20 seconds of preparation (e.g., download of the PSD and pre-scan for optimizing scanning parameters), about 3 seconds to obtain a reference image for ARFI, and about 3 seconds per frequency to generate a focus and measure the resulting tissue displacement (amounting to 27 seconds for 9 frequencies). The total time for determining the optimal frequency for one segment is, thus, less than one minute; efficiency gains can result from a common overhead and a common reference used for all frequencies. (The computational time to process the data is negligible compared with the time for acquiring the measurements.) The total time required for an entire transducer having seven segments is on the order of seven minutes in the above example.

The tissue displacements measured for all segments and frequencies may be stored in an $N_f \times N_s$ array $D_{ij}$, where row i corresponds to frequency $f_i$, and column j corresponds to transducer segment j. If the segments are to be driven at different frequencies, the optimal frequencies are determined by finding the maximum entry i in each column $D_{i\,1}$, $D_{i\,2}$, ... $D_{i\,Ns}$, and selecting frequency $f_i$ for the corresponding segment.

If a single optimum frequency is to be determined for the transducer as a whole, the entries across the columns in each line i (i.e., for each frequency $f_i$) are combined into new values $D_{combined\_i}$ that capture the contributions of all the segments. If different segments are driven at different total powers (e.g., proportional to their respective areas) during the measurements, the individual measured displacements $D_{ij}$ are typically first normalized accordingly. Then, the combined displacements $D_{combined\_i}$ are computed in one of several ways that result in values well-correlated to the combined therapeutic effect of all segments (some, but not all of which have physical interpretations). For example, in some embodiments, the combined displacement value is calculated by summing over the square roots of the individual displacements and squaring the result, yielding a value proportional to the total peak intensity at the focus (provided that the relative phasing between the sub-foci generated with different segments is correct, which can be assured by computer-tomography-based corrections):

$$D_{combined\_i} = \left( \sum_{j=1}^{N_s} \sqrt{D_{ij}} \right)^2$$

In other embodiments, the combined displacement value is simply the sum of the absolute values of individual displacements, and is proportional to the total power applied in the focus region:

$$D_{combined\_i} = \left( \sum_{j=1}^{N_s} |D_{ij}| \right)$$

In yet another embodiment, the L2-norm of the displacement vector $D_i$ is calculated:

$$D_{combined\_i} = \sqrt{\sum_{j=1}^{N_s} (D_{ij})^2}$$

In which manner the combined displacement is calculated may depend, e.g., on which parameter is to be optimized (e.g., peak pressure or total power). The above three embodiments are merely examples; similarly, other norms (or variations that are not norms) may be used as long as they correlate with the combined contribution of the segments. The elements of the combined vector $D_{combined}$ are proportional (or correlated) to the total heat depositions at the various frequencies. Thus, the optimal frequency for the transducer can be determined by identifying the frequency at which the maximum combined displacement will occur. Of course, determining an overall-optimal frequency from measurements taken separately for multiple segments is not limited to measurements of tissue displacement; in embodiments where a parameter other than tissue displacement is used as an indicator for the energy disposition at the target, measurements of this parameters can be similarly combined across segments to find an overall optimum.

The approach described above can be implemented with a suitable computational facility operating in conjunction with one more ultrasound transducers and apparatus (e.g., an MRI apparatus) for measuring the energy deposited at the focus, or another parameter indicative thereof. The computational facility may be implemented in hardware (e.g., circuitry), software, firmware, or any suitable combination thereof, and may be integrated with the ultrasound controller (e.g., control facility 106 of FIG. 1) and/or the imaging apparatus or other device for measuring energy deposition at the target (e.g., image-processing system 216 of FIG. 2), or provided as a separate device in communication therewith.

Figure 8:
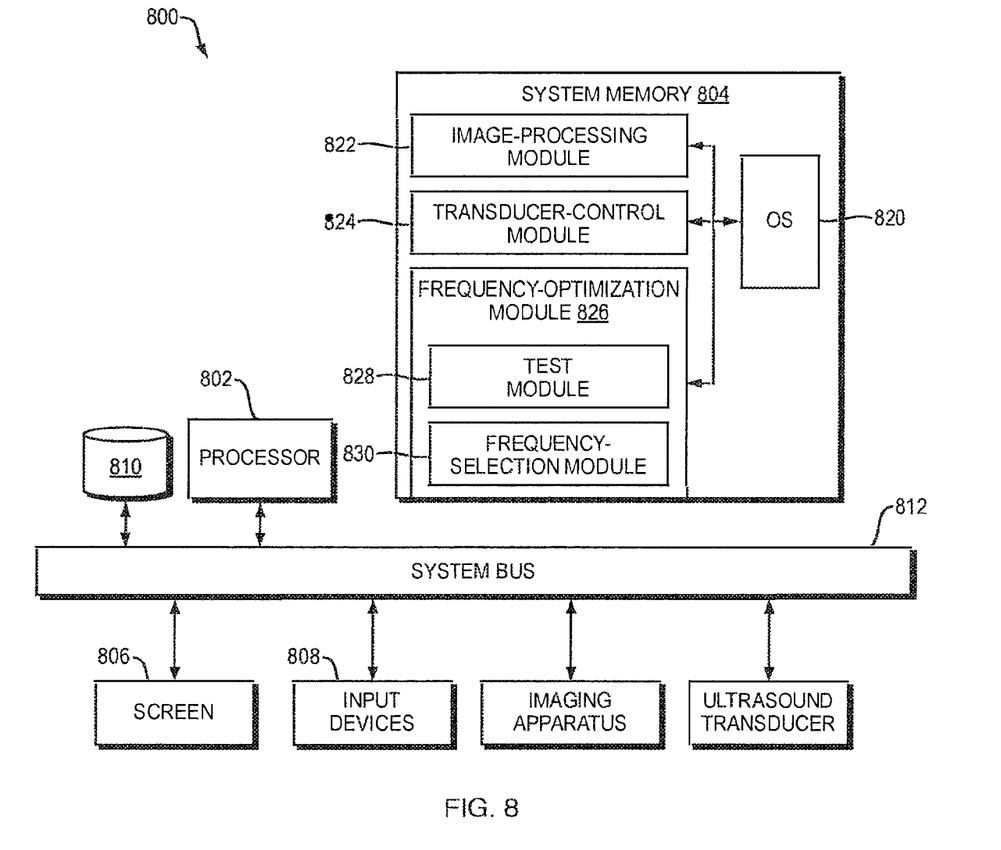
FIG. 8 is a block diagram illustrating a system for optimizing sonication frequency in accordance with various embodiments.

In some embodiments, the computational facility is implemented with a suitably programmed general-purpose computer; FIG. 8 shows an exemplary embodiment. The computer 800 includes one or more processors 802 (e.g., a CPU) and associated system memory 804 (e.g., RAM, ROM, and/or flash memory), user input/output devices (such as a screen 806 and a keyboard, mouse, etc. 808), and typically one or more (typically non-volatile) storage media 810 (e.g., a hard disk, CCD, DVD, USB memory key, etc.) and associates drives. The various components may communicate with each other and with external devices (such as the ultrasound transducer and/or the imaging apparatus) via one or more system buses 812.

The system memory 804 contains instructions, conceptually illustrated as a group of modules, that control the operation of the processor 802 and its interaction with the other hardware components. An operating system 820 directs the execution of low-level, basic system functions such as memory allocation, file management and operation of the peripheral devices. At a higher level, one or more service applications provide the computational functionality required for frequency optimization in accordance herewith. For example, as illustrated, the system may include an image-processing module 822 that allows analyzing images from the MRI (or other imaging) apparatus to identify the target therein and visualize the focus to ensure that it coincides with the target; a transducer-control module 824 for computing the relative phases and amplitudes of the transducer elements based on the target location as well as for controlling ultrasound-transducer operation during both frequency optimization and treatment; and a frequency-optimization module 826 providing functionality to acquire data about the frequency-dependence of the energy absorption at the target and select an optimum frequency (or multiple respective optimum frequencies for various transducer segments) based thereon. More specifically, a test sub-module 828 may determine and/or receive input specifying the test range and test frequencies, direct the transducer-control module 824 to sequentially sonicate the target at these frequencies, and receive and/or analyze image or other data that allows quantifying the energy absorbed at the target for each sonication. Based on this information, a frequency-selection module 830 may determine the frequency or frequencies (for multiple individually optimized segments) that maximize energy absorption at the target, or combine the measurements of the absorption-related parameter across transducer segments (e.g., by computing one of the norms discussed above) to find a frequency that maximizes the overall amount of energy absorbed at the target.

Of course, the depicted organization of the computational functionality into various modules is but one possible way to group software functions; as a person of skill in the art will readily appreciate, fewer, more, or different modules may be used to facilitate frequency-optimization in accordance herewith. However grouped and organized, software may be programmed in any of a variety of suitable programming languages, including, without limitation, C, C++, Fortran, Pascal, Basic, Python, an assembly language, or combinations thereof. Furthermore, as an alternative to software instructions executed by a general-purpose processor, some or all of the functionality may be provided with programmable or hard-wired custom circuitry, including, e.g., a digital signal processor, programmable gate array, application-specific integrated circuit, etc.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. For example, instead of MR-based thermometry or ARFI, any non-invasive imaging technique capable of measuring the (physical or therapeutic) effect of the acoustic beam at the focus may generally be used to select an optimal frequency (or multiple optimal frequencies for different segments) in accordance herewith. Accordingly, the described embodiments are to be considered in all respects as only illustrative and not restrictive.

What is claimed is:

1. A patient-specific frequency-optimization method for ultrasound therapy of a target within the patient, the method comprising:
    defining a plurality of segments within an ultrasound transducer array; and
    separately for each of the segments, driving the segment at each of a plurality of frequencies successively within a test frequency range so as to sonicate the target, and measuring a parameter correlated with an amount of ultrasound energy absorbed in the target for each of the frequencies; and
    for each of the plurality of frequencies, combining values of the parameter measured for the plurality of segments into a total parameter value correlated with a total amount of ultrasound energy absorbed in the target, including combining a first value of the parameter measured for a first of the plurality of segments with a second value of the parameter measured for a second of the plurality of segments; and
    selecting for subsequent focused-ultrasound therapy, among the plurality of frequencies, an optimal frequency corresponding to a value of the measured total parameter that itself corresponds to a maximum total amount of ultrasound energy absorbed in the target, wherein each of the plurality of segments is driven at the optimal frequency during the subsequent focused-ultrasound therapy, and wherein selecting the frequency includes optimizing the frequencies for transducer segments whose acoustic beams pass through tissue regions with different acoustic impedances.

2. The method of claim 1, wherein the parameter is selected from the group consisting of a power, an energy, an intensity, an acoustic force, a tissue displacement, or a temperature.

3. The method of claim 1, wherein the parameter is measured using thermometry.

4. The method of claim 1, wherein the parameters is measured using acoustic radiation force imaging.

5. A system for selecting a patient-specific frequency for ultrasound therapy of a target within the patient, the system comprising:
    an ultrasound transducer comprising a plurality of segments, and an associated controller capable of driving each of the transducer segments at any of a plurality of frequencies within a range of frequencies so as to sonicate the target;
    a measurement facility for measuring a parameter correlated with an amount of ultrasound energy absorbed in the target; and
    a computational facility for (i) causing the ultrasound transducer controller to separately drive each of the segments sequentially at each of a plurality of frequencies within a test range so as to sonicate the target, (ii) causing the measurement facility to measure a parameter correlated with an amount of ultrasound energy absorbed in the target for each of the frequencies, (iii) for each of the plurality of frequencies, combining values of the parameter measured for the plurality of segments into a total parameter value correlated with a total amount of ultrasound energy absorbed in the target, including combining a first value of the parameter measured for a first of the plurality of segments with a second value of the parameter measured for a second of the plurality of segments, and (iv) selecting for subsequent focused-ultrasound therapy, among the plurality of frequencies, an optimal frequency corresponding to a value of the measured total parameter that itself corresponds to a maximum total amount of ultrasound energy absorbed in the target, wherein each of the plurality of segments is driven at the optimal frequency during the subsequent focused-ultrasound therapy, and wherein selecting the frequency includes optimizing the frequencies for transducer segments whose acoustic beams pass through tissue regions with different acoustic impedances.

6. The system of claim 5, wherein the measurement facility comprises a magnetic-resonance imaging apparatus.

7. The system of claim 5, wherein the measured parameter is a tissue displacement.

8. The system of claim 5, wherein the controller is configured to cause the ultrasound transducer, during ultrasound therapy, to drive the segments together at the selected optimal frequency.

* * * * *